United States Patent [19]
Bettarini et al.

[11] Patent Number: 6,136,836
[45] Date of Patent: Oct. 24, 2000

[54] COMPOSITIONS FOR THE SYSTEMIC CONTROL OF PARASITES OF WARM-BLOODED ANIMALS

[75] Inventors: Franco Bettarini, Novara; Paolo Piccardi, Milan, both of Italy

[73] Assignee: Isagro S.p.A., Milan, Italy

[21] Appl. No.: 09/319,261

[22] PCT Filed: Dec. 9, 1997

[86] PCT No.: PCT/EP97/06965

§ 371 Date: Jul. 30, 1999

§ 102(e) Date: Jul. 30, 1999

[87] PCT Pub. No.: WO98/25466

PCT Pub. Date: Jun. 18, 1998

[30] Foreign Application Priority Data

Dec. 12, 1996 [IT] Italy .................................. MI96A2602

[51] Int. Cl.[7] .................................................. A61K 31/415
[52] U.S. Cl. .............................. 514/394; 514/86; 514/89; 514/99; 514/122; 514/131; 514/136; 514/147; 514/343; 514/345; 514/357; 514/404; 514/453; 514/464; 514/467; 514/721; 514/758

[58] Field of Search ...................................... 514/594, 357, 514/404, 345, 721, 467, 464, 89, 86, 122, 453, 136, 131, 758, 99, 147, 343

[56] References Cited

U.S. PATENT DOCUMENTS 5,135,953  8/1992  Potter et al. ............................. 514/594

FOREIGN PATENT DOCUMENTS 271 923  6/1988  European Pat. Off. .

*Primary Examiner*—Rebecca Cook
*Attorney, Agent, or Firm*—Oblon, Spivak, McClelland, Maier & Neustadt, P.C.

[57] ABSTRACT

A composition and method for controlling warm-blooded animal parasites comprising 1-[3-chloro-4-(1,1,2-trifluoro-2-trifluoromethoxyethoxy)phenyl]-3-(2,6,difluorobenzoyl) urea.

19 Claims, No Drawings

COMPOSITIONS FOR THE SYSTEMIC CONTROL OF PARASITES OF WARM-BLOODED ANIMALS

This is a 371 of PCT/EP97/06965 filed Dec. 9, 1997.

The present invention relates to compositions for the systematic control of warm-blooded animal parasites comprising an effective quantity of a particular arylbenzoylurea.

More specifically, the present invention relates to compositions comprising an effective quantity of 1-[3-chloro-4-(1,1,2-trifluoro-2-trifluoromethoxyethoxy)phenyl]-3-(2,6-difluorobenzoyl)urea and a pharmaceutically acceptable carrier and their use for the systematic control of warm-blooded animal parasites.

The present invention also relates to the use of 1-[3-chloro-4-(1,1,2-trifluoro-2-trifluoromethoxyethoxy)phenyl]-3-(2,6-difluorobenzoyl)urea as such for the systemic control of warm-blooded animal parasites.

European patent EP 271.923 describes the compound corresponding to 1-[3-chloro-4-(1,1,2-trifluoro-2-trifluoromethoxyethoxy)phenyl]-3-(2,6-difluorobenzoyl) urea having formula (I):

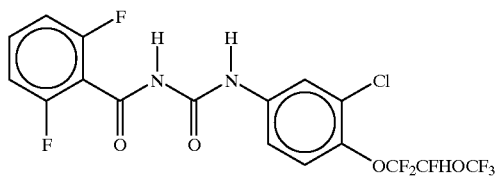

as having a high insecticidal activity.

The above patent also discloses a method for fighting infestations caused by harmful insects which consists in distributing the compound having formula (I), as such or in the form of a suitable composition, onto the surface of the infested area. This method of application is effective for the treatment of agricultural cultivations, basins and waterways, industrial and civil sites, but its utility is limited if the compound having formula (I) is to be adopted in the veterinary and zootechnical field, for example., for protecting domestic animals from these parasites which feed by sucking their host's blood, such as flees, ticks, louse, etc.

The Applicant has now found that the compound having formula (I) is surprisingly effective in protecting warm-blooded animals from ectoparasites and endoparasites, if it is systemically carried into the blood of the animal host as such or, preferably, by means of a suitable pharmaceutically acceptable composition.

In addition, as it has been observed that the compound having formula (I) has a very low oral toxicity, both acute and chronic, on mammals and birds, it does not have mutagen and tetragen effects and does not have the tendency to accumulate in adipose tissues, the use of this compound having formula (I), as well as being particularly effective, is also safe and harmless for the animals treated.

The present invention therefore relates to compositions comprising an effective quantity of 1-[3-chloro-4-(1,1,2-trifluoro-2-trifluoromethoxyethoxy)phenyl] 3-(2,6-difluorobenzoyl)urea having formula (I):

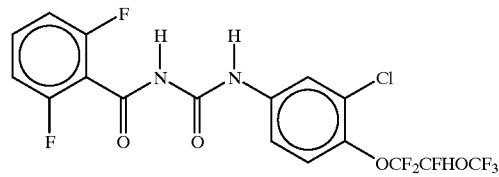

and a pharmaceutically acceptable carrier.

The above compositions can be used for the systemic control of warm-blooded animal parasites.

The compound having formula (I) can be prepared by means of a process which comprises the reaction of 3-chloro-4-(1,1,2-trifluoro-2-trifluoromethoxyethoxy)-aniline having formula (II):

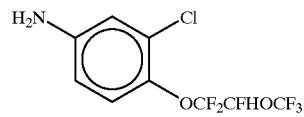

with 2,6-difluorobenzoylisocyanate having formula (III):

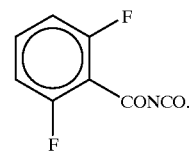

Alternatively, the compound having formula (I) can be prepared by a process which comprises the reaction of 3-chloro-4-(1,1,2-trifluoro-2-trifluoromethoxyethoxy) phenylisocyanate having formula (IV):

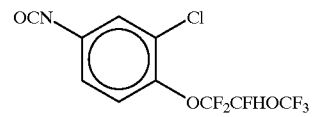

with 2,6-difluorobenzamide having formula (V):

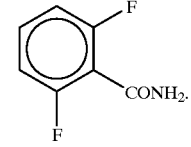

The above processes are carried out in an anhydrous environment and in the presence of an inert solvent, at a temperature ranging from 0° C. and the boiling point of the reaction mixture.

Examples of inert solvents suitable for the purpose are aromatic hydrocarbons such as, for example, benzene, toluene, xylene, chlorobenzene; chlorinated hydrocarbons such as, for example, methylene chloride, chloroform, carbon tetrachloride, dichloroethane; ethers such as, for example, diisopropylether, tetrahydrofuran, dioxane.

The compounds having formula (III) and (V) can be prepared according to methods which are well known in literature. The compound having formula (V) is also commercially available.

The compound having formula (II) can be prepared as described, for example, in European patent EP 271.923.

The compound having formula (IV) can be prepared starting from the compound having formula (II) and phosgene, operating according to an analogous procedure to that described, for example, by Blatt in: "Organic Synthesis" (1959), Collective Vol. 2, pages 453–455, John Wiley Ed., New York.

Carriers which can be used for the purposes of the present invention can be liquids or solids according to the method of administration. In fact, the above compositions can be administered in any form which allows them to be introduced into the blood of the animal to be protected such as, for example, orally or by percutaneous administration.

Carriers which are suitable for the purpose are those which do not have harmful effects on the animals to be treated and which do not negatively influence the method of application or the desired results.

Examples of liquid carriers which can be used for the purposes of the present invention are: water, N-methylpyrrolidone, vegetable oil, glycols, etc.

Examples of solid carriers which can be used for the present invention are: talc, clay, molasses in powder form, cellulose and its derivatives, lactose, starch, colloidal silica, magnesium stearate, stearic acid, etc.

The compound having formula (I) can also be administered to the animals to be treated as such.

The use of 1-[3-chloro-4-(1,1,2-trifluoro-2-trifluoromethoxyethoxy)phenyl]-3-(2,6-difluorobenzoyl) urea having formula (I):

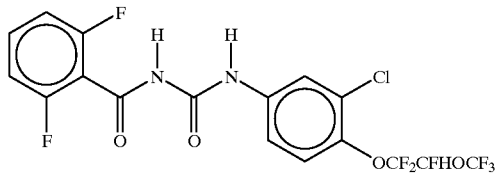

(I)

is therefore included in the scope of the present invention for the systemic control of warm-blooded animal parasites.

The oral administration can be carried out by mixing the compound having formula (I), as such or formulated with a suitable carrier, in the food or drinking water, or administering it in the form of long drinks, tablets, capsules, etc.

When the compound having formula (I) is administered as an additive to the food of animals, it is convenient to prepare a "premix" in which the compound having formula (I) is dispersed in a liquid or solid carrier. The "premix" is then dispersed in the food using, for example, a conventional mixer.

When the compound having formula (I) is administered as an additive to drinking water or as a long drink, it is convenient to use a suspendible formulation. This formulation can be, for example, a concentrated suspension which is mixed with the water or a dry preparation which is mixed and suspended in the water. In both cases, it is preferable to have the compound having formula (I) in a finely pulverized form.

The compound having formula (I) can be easily formulated into capsules or tablets, according to the methods traditionally used in pharmaceutical practice. Gelatine capsules contain the active principle (compound having formula (I), in the present case) and solid carriers such as, for example, colloidal silica, lactose, starch, derivatives of cellulose, magnesium stearate, stearic acid and the like. These carriers can also be used to make tablets. Both tablets and capsules can be produced as drugs with controlled release in order to provide a continuous release of the active principle for a certain period, for example, several hours.

The percutaneous administration, can be conveniently carried out by means of subcutaneous, dermal, intermuscular or intravenous injection according to the methods normally used in pharmaceutical and veterinary practice.

The percutaneous administration can also be carried out by absorption of the compound having formula (I) through the epidermis of the animal to be treated. This absorption takes place as a result of surface treatment of the animal to be treated by immersion, wetting, spraying, powdering, smearing, etc.

When the percutaneous administration is carried out by injection, an injectable suspension can be conveniently prepared by suspending the compound having formula (I), in the form of fine powder, in a formulation of pharmaceutically acceptable liquid carriers. Liquid carriers which can be used for the purpose are, for example, vegetable oils such as peanut oil, corn oil, etc; glycols such as polyethylene glycols, etc; water, etc.

In the injectable suspensions as well as in suspensions administered in long drinks or in drinking water, it may be necessary to have the presence of physiologically compatible adjuvants such as, for example, emulsifying agents, suspending agents, dispersers, thickners, surface-active agents, etc.

Examples of emulsifying agents which can be used for the purpose are: salts of dodecylbenzenesulfonate and toluenesulfonate, adducts of ethylene oxide and alkylphenols, esters of oleic acid or stearic acid, etc.

Examples of dispersers which can be used for the purpose are: salts of naphthalenesulfonate, lignin sulfonates, sulfates of fatty alcohols, etc.

Examples of thickners which can be used for the purpose are: carboxymethylcellulose, polyvinylpyrrolidone, gelatine, alginates, etc.

Examples of surface-active agents which can be used are: lecithin, esters of polyoxyethylene sorbitan, etc.

The compositions of the present invention can contain, addition to the compound having formula (I), other antiparasitic agents such as, for example, other insecticides, acaricides, anthelminthics, etc.

Examples of insecticides and/or acaricides which can be used for the purposes of the present invention are: chlorpyrifos, coumaphos, dichlorvos, diazinon, dimethoate, fenthion, malathion and other phosphorganic products; lindane, nicotine, rotenone, natural pyretrines and synthetic pyretroids; avermectine, milbemicine and their derivatives, fenoxycarb, pyriproxyfen, diofenolan, 1-(5-chloro-4-pentinyloxy)-4-phenoxybenzene and other products with a young hormone activity; imidacloprid, acetamiprid, nitenpyram, fipronil.

The compositions of the present invention can contain, in addition to the compound having formula (I), other biologically active substances such as, for example, medicines, growth promoters, vitamins, mineral salts, etc.

Warm-blooded animal parasites which can be effectively controlled using the compositions of the present invention or the compound having formula (I) as such are the following:

mites belonging to the suborders Mesostigmata, Sarcoptiformes, Trombidiformes and Onchychopalpida;

louse belonging to the orders Anoplura and Mallophaga;

ticks belonging to the Ixodidae and Argasidae families;

fleas belonging to the Pulicidae and Ceratophyllidae families;

bugs of various types;

Triatoma and other Heteroptera;

diptera belonging to the suborders Brackycera, Cyclorrhapha and Nematocera;

helminths belonging to the Nematoda, Acantocephala, Cestoidea, Trematoda groups;

protozoa belonging to the order Coccidia and to the Trypanosomatidae, Trichomonadidae and Endamoebidae families.

Warm-blooded animals which can be treated using the compositions of the present invention or the compound having formula (I) as such are, apart from human beings, domestic animals such as cattle, horses, sheep, goats, poultry, pigs, dogs and cats.

The present invention also relates to the use of the above compositions for the systemic control of warm-blooded animals.

The dosage of the compound having formula (I), whether it be administered as such or using the above compositions, can vary depending on various factors such as the means of administration, the type and degree of infestation, the age, state of health, body weight of the animal to be treated, the frequency of the treatment, desired effects. Dosages of the compound having formula (I) generally between 0.01 mg and 1000 mg per kg of the body weight of the animal to be treated, preferably between 0.1 mg and 100 mg per kg of body weight, are sufficient to eradicate the parasites without prejudicing the health of the animals treated.

Some illustrative examples are provided for a better understanding of the invention and for its embodiment, but do not restrict the scope of the invention in any way.

EXAMPLE 1

Preparation of 3-chloro-4-(1,1,2-trifluoro-2-trifluoromethoxyethoxy)aniline having Formula (II)

Perfluoromethylvinylether (1.66 g, 10 mmoles), in a mixture consisting of 2-chloro-4-aminophenol (1.44 g, 10 mmoles), dimethylsulfoxide (20 ml), toluene (20 ml) and potassium carbonate in powder form at 85% (100 mg) is bubbled into a 100 ml flask, under nitrogen, at 0° C.

The mixture is maintained under stirring at 0° C. for 3.5 hours. Water (100 ml) is subsequently poured in and the mixture is extracted with ethyl ether. The organic extract is anhydrified with sodium sulfate, filtered and concentrated to give 3 g of aniline having formula (II).

The spectrometric analysis gave the following results: $^1$H-NMR (CDCl$_3$): 7.28–6.4 (m, 3H); 6.3–5.69 (dt, 1H); 3.58 (bs, 2H).

EXAMPLE 2

Preparation of 1-[3-chloro-4-(1,1,2-trifluoro-2-trifluoromethoxyethoxy)phenyl]-3-(2,6-difluorobenzoyl)urea [Compound (I)].

The aniline having formula (II) (22.7 g, 73.3 mmoles), obtained as described in Example 1, is dissolved in anhydrous chlorobenzene (60 ml), in a 500 ml flask maintained under a nitrogen atmosphere.

A solution of 2,6-difluorobenzoylisocyanate having formula (III) (13.4 g, 73.3 mmoles) in anhydrous chlorobenzene (40 ml) is added dropwise to the above solution, maintaining the whole mixture under stirring, at room temperature.

The stirring is continued for 12 hours after heating to 100° C. The mixture is subsequently cooled to 0° C. and the solid which is formed is filtered. The solid is then washed with cold hexane and dried under nitrogen.

30.5 g of Compound (I) are obtained (61.92 mmoles) with a melting point of 172° C.–174° C.

EXAMPLE 3

Formulation of Compound (I) as Diet Additive

A solid mixture is prepared consisting of Compound (I), obtained as described in Example 2, and clay in the following weight percentages:

5% of Compound (I);

95% of clay.

The above mixture is then finely pulverized and remixed by grinding. The composition thus obtained is then mixed with the food forming the diet of the animals to be treated.

EXAMPLE 4

Formulation of Compound (I) in Tablet-form.

Following the conventional procedures, tablets are prepared each containing Compound (I) in a finely pulverized form (100 mg), colloidal silica (0.2 mg), magnesium stearate (5 mg), microcrystalline cellulose (275 mg), starch (11 mg) and lactose (98.8 mg).

Tablets containing dosages of between 20 mg and 200 mg of active principle can be analogously prepared.

EXAMPLE 5

Preparation of Compound (I) in Gelatine Capsules.

Standard capsules consisting of two parts of hard gelatine, are filled with a mixture of lactose (150 mg), cellulose (50 mg), magnesium stearate (6 mg) and Compound (I) in a finely pulverized form (25 mg).

Capsules containing the active principle in quantities varying from 5 mg to 50 mg can be analogously prepared.

EXAMPLE 6

Systemic Activity of Compound (I) for Controlling Fleas.

Four dogs are infested with fleas belonging to the species *Ctenocephalides felis* and subdivided into two groups of two individuals.

One group (C1 and C2) is treated for 10 consecutive days with a daily dosage of 5 mg/kg of body weight of Compound (I) administered orally by the addition to the daily diet of the composition obtained as described in Example 3.

The second group of dogs (C3 and C4) is used as a control and is fed with the same diet as the first group but without the addition of Compound (I).

After 3, 8 and 10 days of treatment the eggs of the fleas used for the infestation, are collected on sheets of paper placed under the cages where the dogs are kept for the whole duration of the treatment. The eggs are counted, placed on an artificial culture medium and incubated. The number of pupae and adults of fleas which emerge is determined and indicated in Table 1.

| | Days after treatment | | | | | | | | |
|---|---|---|---|---|---|---|---|---|---|
| | 3 | | | 8 | | | 10 | | |
| Animal | u(1) | p(2) | a(3) | u(1) | p(2) | a(3) | u(1) | p(2) | a(3) |
| C1 | 328 | 0 | 0 | 126 | 0 | 0 | 73 | 0 | 0 |
| C2 | 206 | 0 | 0 | 18 | 0 | 0 | 13 | 0 | 0 |
| C3 | 520 | 338 | 322 | 339 | 263 | 241 | 148 | 137 | 122 |
| C4 | 930 | 539 | 358 | 527 | 430 | 398 | 301 | 258 | 208 |

$u^{(1)}$: eggs
$p^{(2)}$: pupae
$a^{(3)}$: adults

What is claimed is:

1. A composition suitable for the systemic control of warm-blooded animal parasites, comprising:
an effective amount of 1-[3-chloro-4-(1,1,2-trifluoro-2-trifluoromethoxyethoxy)phenyl]-3-(2,6-difluorobenzoyl) urea represented by formula (I):

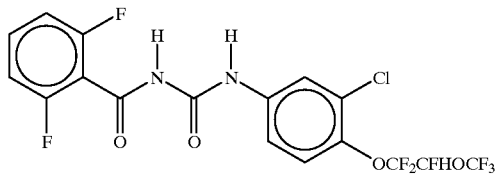

at least one additional antiparasitic agent, and
a pharmaceutically acceptable liquid or solid carrier,
wherein
the liquid carrier is selected from the group consisting of water, N-methylpyrrolidone, vegetable oils, and glycols, and
the solid carrier is selected from the group consisting of talc, clay, molasses in powder form, cellulose and derivatives thereof, lactose, starch, colloidal silica, magnesium stearate, and stearic acid.

2. The composition of claim 1, wherein the additional antiparasitic agent is an insecticide, acaricide or anthelminthic.

3. The composition of claim 2, wherein the additional antiparasitic agent is an insecticide or an acaricide which is selected from the group consisting of chloropyrifos, coumaphos, dichlorvos, diazinon, dimethoate, fenthion, malathion, lindane, nicotine, rotenone, natural pyretrines, synthetic pyretroids, avermectine, milbemicine and derivatives thereof, fenoxycarb, pyriproxyfen, diofenolan, 1-(5-chloro-4-pentinyloxy)-4-phenoxybenzene, imidacloprid, acetamiprid, nitenpyram, and fipronil.

4. The composition of claim 1, further comprising at least one biologically active substance selected from the group consisting of growth promoters, vitamins, and mineral salts.

5. The composition of claim 1, which comprises the liquid carrier.

6. The composition of claim 1, which comprises the solid carrier.

7. The composition of claim 1, wherein the liquid carrier is selected from the group consisting of N-methylpyrrolidone, vegetable oils, and glycols.

8. A method of systemically controlling parasites on a warm-blooded animal, comprising administering to a warm-blooded animal an effective amount of a compound represented by formula (I):

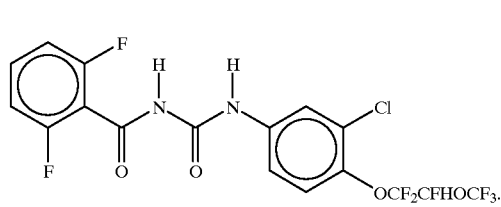

9. The method of claim 8, wherein the arm-blooded animal is selected from human beings, cattle, horses, sheep, goats, poultry, pigs, dogs and cats.

10. The method of claim 8, wherein the composition of formula (I) is administered in the form of a composition, wherein the composition additionally comprises a pharmaceutically acceptable liquid or solid carrier.

11. The method of claim 10, wherein the liquid carrier is selected from the group consisting of water, N-methylpyrrolidone, vegetable oils, and glycols.

12. The method of claim 10, wherein the solid carrier is selected from the group consisting of talc, clay, molasses in powder form, cellulose and derivatives thereof, lactose, starch, colloidal silica, magnesium stearate, and stearic acid.

13. The method of claim 8, wherein the composition further comprises at least one additional antiparasitic agent.

14. The method of claim 13, wherein the additional antiparasitic agent is an insecticide, acaricide or anthelminthic.

15. The method of claim 14, wherein the additional antiparasitic agent is an insecticide or an acaricide which is selected from the group consisting of chloropyrifos, coumaphos, dichlorvos, diazinon, dimethoate, fenthion, malathion, lindane, nicotine, rotenone, natural pyretrines, synthetic pyretroids, avermectine, milbemicine and derivatives thereof, fenoxycarb, pyriproxyfen, diofenolan, 1-(5-chloro-4-pentinyloxy)-4-phenoxybenzene, imidacloprid, acetamiprid, nitenpyram, and fipronil.

16. The method of claim 8, wherein the composition further comprises at least one biologically active substance selected from the group consisting of growth promoters, vitamins, and mineral salts.

17. The method of claim 8, wherein the composition comprises the liquid carrier.

18. The method of claim 8, wherein the composition comprises the solid carrier.

19. The method of claim 17, wherein the liquid carrier is selected from the group consisting of N-methylpyrrolidone, vegetable oils, and glycols.

* * * * *